United States Patent
Goorden et al.

(10) Patent No.: US 10,303,064 B2
(45) Date of Patent: May 28, 2019

(54) RADIATION CONDITIONING SYSTEM, ILLUMINATION SYSTEM AND METROLOGY APPARATUS, DEVICE MANUFACTURING METHOD

(71) Applicant: ASML Netherlands B.V., Veldhoven (NL)

(72) Inventors: Sebastianus Adrianus Goorden, Eindhoven (NL); Teunis Willem Tukker, Eindhoven (NL); Johannes Matheus Marie De Wit, Helmond (NL); Jonas Mertes, Eindhoven (NL); Gerbrand Van Der Zouw, Waalre (NL)

(73) Assignee: ASML Netherlands B.V., Veldhoven (NL)

( * ) Notice: Subject to any disclaimer, the term of this patent is extended or adjusted under 35 U.S.C. 154(b) by 40 days.

(21) Appl. No.: 15/589,958

(22) Filed: May 8, 2017

(65) Prior Publication Data

US 2017/0329232 A1 Nov. 16, 2017

(30) Foreign Application Priority Data

May 11, 2016 (EP) .................................. 16169199

(51) Int. Cl.
*G03B 27/42* (2006.01)
*G03F 7/20* (2006.01)
(Continued)

(52) U.S. Cl.
CPC ...... *G03F 7/70191* (2013.01); *G01B 11/0608* (2013.01); *G01B 11/272* (2013.01);
(Continued)

(58) Field of Classification Search
CPC ............. G03F 7/70091; G03F 7/70191; G03F 7/70575; G03F 7/70075; G03F 7/70141;
(Continued)

(56) References Cited

U.S. PATENT DOCUMENTS 5,473,408 A 12/1995 Hoffman et al.
5,601,733 A 2/1997 Partlo
(Continued)

FOREIGN PATENT DOCUMENTS

EP 1 944 653 A2 7/2008
EP 2 253 997 A2 11/2010
(Continued)

OTHER PUBLICATIONS

International Search Report and Written Opinion of the International Searching Authority directed to related International Patent Application No. PCT/EP2017/060736, dated Jul. 31, 2017; 16 pages.

*Primary Examiner* — Mesfin T Asfaw
(74) *Attorney, Agent, or Firm* — Sterne, Kessler, Goldstein & Fox P.L.L.C.

(57) ABSTRACT

Disclosed are an optical system for conditioning a beam of radiation, and an illumination system and metrology apparatus comprising such an optical system. The optical system comprises one or more optical mixing elements in an optical system. The optical system defines at least a first optical mixing stage, at least a second optical mixing stage, and at least one transformation stage, configured such that radiation entering the second optical mixing stage includes a transformed version of radiation exiting the first optical mixing stage. The first and second optical mixing stages can be provided using separate optical mixing elements, or by multiple passes through the same optical mixing element. The transformation stage can be a Fourier transformation (Continued)

stage. Both spatial distribution and angular distribution of illumination can be homogenized as desired.

20 Claims, 6 Drawing Sheets

(51) Int. Cl.
   *G03F 7/16*      (2006.01)
   *G03F 7/38*      (2006.01)
   *G03F 7/26*      (2006.01)
   *G01B 11/06*     (2006.01)
   *G01B 11/27*     (2006.01)
   *G01N 21/88*     (2006.01)
   *G01N 21/47*     (2006.01)
   *G02B 27/09*     (2006.01)

(52) U.S. Cl.
   CPC ..... *G01N 21/4738* (2013.01); *G01N 21/8851* (2013.01); *G02B 27/0994* (2013.01); *G03F 7/16* (2013.01); *G03F 7/20* (2013.01); *G03F 7/26* (2013.01); *G03F 7/38* (2013.01); *G03F 7/70075* (2013.01)

(58) Field of Classification Search
   CPC ............. G03F 7/70558; G03F 7/70133; G03F 7/70308; G21K 1/10
   See application file for complete search history.

(56) References Cited

U.S. PATENT DOCUMENTS

| | | | |
|---|---|---|---|
| RE39,846 E * | 9/2007 | Tanitsu | ........................... 355/53 |
| 2003/0053217 A1 | 3/2003 | Mori | |
| 2004/0263817 A1 | 12/2004 | Tanitsu et al. | |
| 2010/0266268 A1 | 10/2010 | Jennings et al. | |
| 2012/0123581 A1* | 5/2012 | Smilde | ................ G03F 7/70483 |
| | | | 700/105 |
| 2012/0212724 A1* | 8/2012 | Osaka | ................... G03F 7/7005 |
| | | | 355/70 |
| 2014/0028985 A1* | 1/2014 | Janssens | ................ G02B 27/48 |
| | | | 353/31 |
| 2015/0003103 A1* | 1/2015 | Tukker | ............... G02B 27/0927 |
| | | | 362/551 |

FOREIGN PATENT DOCUMENTS

| | | |
|---|---|---|
| WO | WO 2007/137763 A2 | 12/2007 |
| WO | WO 2017/144265 A1 | 8/2017 |

* cited by examiner

RADIATION CONDITIONING SYSTEM, ILLUMINATION SYSTEM AND METROLOGY APPARATUS, DEVICE MANUFACTURING METHOD

BACKGROUND

Field of the Invention

The present invention relates to methods and apparatus for conditioning beams of radiation. Such apparatus can be used in an illumination system usable in metrology apparatus usable, for example, in the manufacture of devices by lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, a measure of the accuracy of alignment of two layers in a device. Overlay may be described in terms of the degree of misalignment between the two layers, for example reference to a measured overlay of 1 nm may describe a situation where two layers are misaligned by 1 nm.

Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target by iterative approaches such as rigorous coupled wave analysis or finite element methods; library searches; and principal component analysis.

In metrology, and particularly metrology using scatterometers, the homogeneity of the beam of radiation used for the measurement is important. Therefore it is desirable to improve homogeneity of such a beam and/or control thereof.

In U.S. provisional patent application 62/299,723, not published at the priority date of the present application, it is proposed to use a so-called chaotic mixing rod as an optical mixing element to homogenize illumination in a metrology apparatus such as a scatterometer. The chaotic mixing rod may have a form similar to ones disclosed for use in LED lighting, in published patent application US 2015/0003103 A1. The chaotic mixing rod effectively homogenizes the spatial distribution of radiation across the illuminating beam. For demanding applications such as in metrology, homogeneity of angular distribution (ray direction) would be desirable, not only spatial distribution. The provisional patent application 62/299,723 proposes to use a filter element in a pupil plane of the optical system, to modulate the angular distribution of radiation, before it enters the mixing rod.

SUMMARY OF THE INVENTION

The present invention aims to provide an alternative form of homogenizer, for conditioning a beam of radiation to have a desired angular distribution. The desired angular distribution may be uniform (homogenized), or some other non-uniform angular distribution.

The invention in a first aspect provides a system for conditioning a beam of radiation, the system defining a path for a beam of radiation, the path including at least a first mixing stage, at least a second mixing stage, and at least one transformation stage, configured such that radiation entering the second mixing stage includes a transformed version of radiation exiting the first mixing stage.

By including a transformation stage between the mixing stages, a homogenized spatial distribution obtained in the first mixing stage can for example be transformed into a homogenized angular distribution, before entry into the second mixing stage. Homogenization of the beam after them second mixing stage is then more complete.

Various embodiments of the system can be envisaged to implement the various stages. Each mixing stage can be provided by a different mixing element (for example a chaotic mixing rod). Alternatively, the optical path may pass two or more times through a common mixing element, to define the different mixing stages.

While the invention will be illustrated by examples employing optical radiation in the contexts of lithography and/or metrology, the radiation is not limited to optical radiation, and could for example be acoustic (sound) radiation.

The invention in a second aspect system for conditioning a beam of radiation, the system defining a path for a beam of radiation, the path including at least a first mixing stage and at least a second mixing stage, wherein said first mixing stage and said second mixing stage are provided by at least one common mixing element, said system being arranged to deliver at least a portion of radiation exiting the first mixing stage back into the common mixing element to enter the second mixing stage.

The invention further provides a metrology apparatus comprising:

an illumination system for delivering inspection radiation to a structure under inspection; and a detection system configured to detect radiation arising from interaction of the structure with said inspection radiation, wherein the illumination system includes a radiation conditioning system according to the first and/or second aspect of the invention as set forth above.

The invention further provides a method of measuring a property of a structure, the method comprising:

delivering inspection radiation to a structure under inspection; and detecting radiation arising from interaction of the structure with said inspection radiation; and determining a measurement of said property of the structure based on properties of the detected radiation, wherein the inspection radiation is conditioned using a radiation conditioning system according to the first and/or second aspect of the invention as set forth above.

The invention yet further provides a method of manufacturing devices wherein a device pattern is applied to a series of substrates using a lithographic process, the method including measuring a property of at least one structure formed as part of or beside said device pattern on at least one of said substrates using a measuring method according to the invention set forth above, and controlling the lithographic process for later substrates in accordance with the result of the method.

The invention yet further provides a lithographic apparatus comprising:

an illumination system for delivering radiation to a patterning device; and a projection system for using said radiation to transfer a pattern from the patterning device to a substrate, wherein said illumination system includes a radiation conditioning system according to the first and/or second aspect of the invention as set forth above.

The invention yet further provides a method of manufacturing devices wherein a device pattern is applied to a substrate using a lithographic apparatus according to the invention as set for the above, and one or more chemical and/or physical processing steps are applied to the substrate to form functional device features in accordance with the applied pattern.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying drawings in which.

DETAILED DESCRIPTION OF EXEMPLARY EMBODIMENTS

Before describing embodiments of the invention in detail, it is instructive to present an example environment in which embodiments of the present invention may be implemented.

Figure 1:
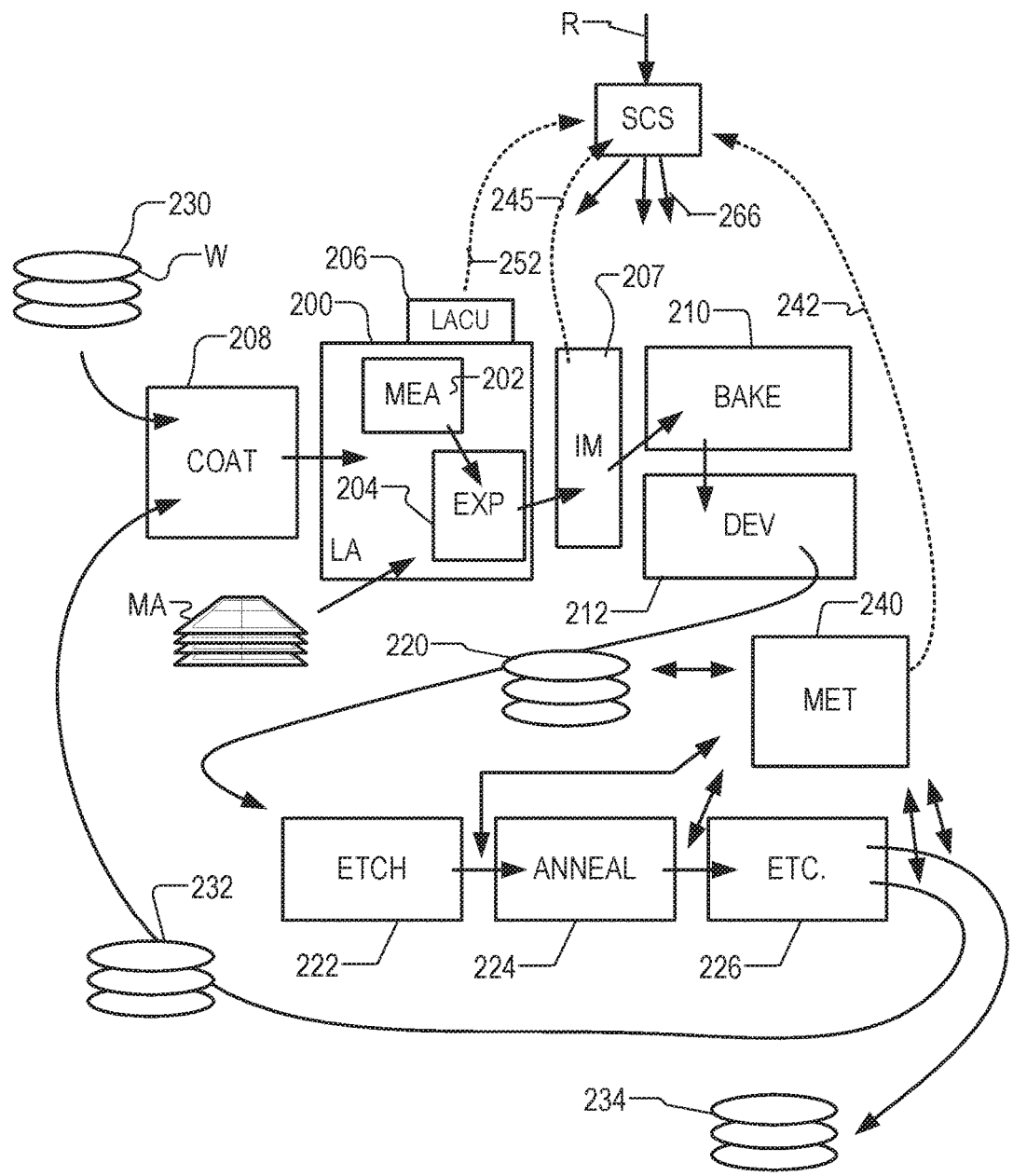
FIG. 1 depicts a lithographic apparatus together with other apparatuses forming a production facility for semiconductor devices.

FIG. 1 at 200 shows a lithographic apparatus LA as part of an industrial facility implementing a high-volume, lithographic manufacturing process. In the present example, the manufacturing process is adapted for the manufacture of semiconductor products (integrated circuits) on substrates such as semiconductor wafers. The skilled person will appreciate that a wide variety of products can be manufactured by processing different types of substrates in variants of this process. The production of semiconductor products is used purely as an example which has great commercial significance today.

Within the lithographic apparatus (or "litho tool" 200 for short), a measurement station MEA is shown at 202 and an exposure station EXP is shown at 204. A control unit LACU is shown at 206. In this example, each substrate visits the measurement station and the exposure station to have a pattern applied. In an optical lithographic apparatus, for example, a projection system is used to transfer a product pattern from a patterning device MA onto the substrate using conditioned radiation and a projection system. This is done by forming an image of the pattern in a layer of radiation-sensitive resist material.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. The patterning MA device may be a mask or reticle, which imparts a pattern to a radiation beam transmitted or reflected by the patterning device. Well-known modes of operation include a stepping mode and a scanning mode. As is well known, the projection system may cooperate with support and positioning systems for the substrate and the patterning device in a variety of ways to apply a desired pattern to many target portions across a substrate. Programmable patterning devices may be used instead of reticles having a fixed pattern. The radiation for example may include electromagnetic radiation in the deep ultraviolet (DUV) or extreme ultraviolet (EUV) wavebands. The present disclosure is also applicable to other types of lithographic process, for example imprint lithography and direct writing lithography, for example by electron beam.

The lithographic apparatus control unit LACU which controls all the movements and measurements of various actuators and sensors to receive substrates W and reticles MA and to implement the patterning operations. LACU also includes signal processing and data processing capacity to implement desired calculations relevant to the operation of the apparatus. In practice, control unit LACU will be realized as a system of many sub-units, each handling the real-time data acquisition, processing and control of a sub-system or component within the apparatus.

Before the pattern is applied to a substrate at the exposure station EXP, the substrate is processed in at the measurement station MEA so that various preparatory steps may be carried out. The preparatory steps may include mapping the surface height of the substrate using a level sensor and measuring the position of alignment marks on the substrate using an alignment sensor. The alignment marks are arranged nominally in a regular grid pattern. However, due to inaccuracies in creating the marks and also due to deformations of the substrate that occur throughout its processing, the marks deviate from the ideal grid. Consequently, in addition to measuring position and orientation of the substrate, the alignment sensor in practice must measure in detail the positions of many marks across the substrate area, if the apparatus is to print product features at the correct locations with very high accuracy. The apparatus may be of a so-called dual stage type which has two substrate tables, each with a positioning system controlled by the control unit LACU. While one substrate on one substrate table is being exposed at the exposure station EXP, another substrate can be loaded onto the other substrate table at the measurement station MEA so that various preparatory steps may be carried out. The measurement of alignment marks is therefore very time-consuming and the provision of two substrate tables enables a substantial increase in the throughput of the apparatus. If the position sensor IF is not capable of measuring the position of the substrate table while it is at the measurement station as well as at the exposure station, a second position sensor may be provided to enable the positions of the substrate table to be tracked at both stations. Lithographic apparatus LA may for example be of a so-called dual stage type which has two substrate tables and two stations—an exposure station and a measurement station—between which the substrate tables can be exchanged.

Within the production facility, apparatus 200 forms part of a "litho cell" or "litho cluster" that contains also a coating apparatus 208 for applying photosensitive resist and other coatings to substrates W for patterning by the apparatus 200. At an output side of apparatus 200, a baking apparatus 210 and developing apparatus 212 are provided for developing the exposed pattern into a physical resist pattern. Between all of these apparatuses, substrate handling systems take care of supporting the substrates and transferring them from one piece of apparatus to the next. These apparatuses, which are often collectively referred to as the track, are under the control of a track control unit which is itself controlled by a supervisory control system SCS, which also controls the lithographic apparatus via lithographic apparatus control unit LACU. Thus, the different apparatus can be operated to maximize throughput and processing efficiency. Supervisory control system SCS receives recipe information R which provides in great detail a definition of the steps to be performed to create each patterned substrate.

Once the pattern has been applied and developed in the litho cell, patterned substrates 220 are transferred to other processing apparatuses such as are illustrated at 222, 224, 226. A wide range of processing steps is implemented by various apparatuses in a typical manufacturing facility. For the sake of example, apparatus 222 in this embodiment is an etching station, and apparatus 224 performs a post-etch annealing step. Further physical and/or chemical processing steps are applied in further apparatuses, 226, etc. Numerous types of operation can be required to make a real device, such as deposition of material, modification of surface material characteristics (oxidation, doping, ion implantation etc.), chemical-mechanical polishing (CMP), and so forth. The apparatus 226 may, in practice, represent a series of different processing steps performed in one or more apparatuses.

As is well known, the manufacture of semiconductor devices involves many repetitions of such processing, to build up device structures with appropriate materials and patterns, layer-by-layer on the substrate. Accordingly, substrates 230 arriving at the litho cluster may be newly prepared substrates, or they may be substrates that have been processed previously in this cluster or in another apparatus entirely. Similarly, depending on the required processing, substrates 232 on leaving apparatus 226 may be returned for a subsequent patterning operation in the same litho cluster, they may be destined for patterning operations in a different cluster, or they may be finished products to be sent for dicing and packaging.

Each layer of the product structure requires a different set of process steps, and the apparatuses 226 used at each layer may be completely different in type. Further, even where the processing steps to be applied by the apparatus 226 are nominally the same, in a large facility, there may be several supposedly identical machines working in parallel to perform the step 226 on different substrates. Small differences in set-up or faults between these machines can mean that they influence different substrates in different ways. Even steps that are relatively common to each layer, such as etching (apparatus 222) may be implemented by several etching apparatuses that are nominally identical but working in parallel to maximize throughput. In practice, moreover, different layers require different etch processes, for example chemical etches, plasma etches, according to the details of the material to be etched, and special requirements such as, for example, anisotropic etching.

The previous and/or subsequent processes may be performed in other lithography apparatuses, as just mentioned, and may even be performed in different types of lithography apparatus. For example, some layers in the device manufacturing process which are very demanding in parameters such as resolution and overlay may be performed in a more advanced lithography tool than other layers that are less demanding. Therefore some layers may be exposed in an immersion type lithography tool, while others are exposed in a 'dry' tool. Some layers may be exposed in a tool working at DUV wavelengths, while others are exposed using EUV wavelength radiation.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which litho cell LC is located may also include one or more metrology systems. The metrology systems may include a stand-alone metrology apparatus MET 240 and/or an integrated metrology apparatus IM 207. The stand-alone metrology apparatus MET 240 receives some or all of the substrates W that have been processed in the litho cell for performing measurements offline. The integrated metrology apparatus IM 207 performs inline measurements and is integrated into the track to receive and measure some or all of the substrates W immediately after exposure. Metrology results are provided directly or indirectly to the supervisory control system (SCS) 238. If errors are detected, adjustments may be made to exposures of subsequent substrates, especially if the metrology can be done soon and fast enough that other substrates of the same batch are still to be exposed.

A common example of a metrology apparatus in a modern lithographic production facility is a scatterometer, for example an angle-resolved scatterometer or a spectroscopic scatterometer, and it may normally be applied to measure properties of the developed substrates at 220 prior to etching in the apparatus 222. Using stand-alone metrology apparatus 240 and/or integrated metrology apparatus 207, it may be determined, for example, that important performance parameters such as overlay or critical dimension (CD) do not meet specified accuracy requirements in the developed resist. Prior to the etching step, the opportunity exists to strip the developed resist and reprocess the substrates 220 through the litho cluster. As is also well known, the metrology results 242 from the apparatus 240 can be used to maintain accurate performance of the patterning operations in the litho cluster, by supervisory control system SCS and/or control unit LACU 206 making small adjustments over time, thereby minimizing the risk of products being made out-of-specification, and requiring re-work. Of course, metrology apparatus 240 and/or other metrology apparatuses (not shown) can be applied to measure properties of the processed substrates 232, 234, and incoming substrates 230.

Figure 2:
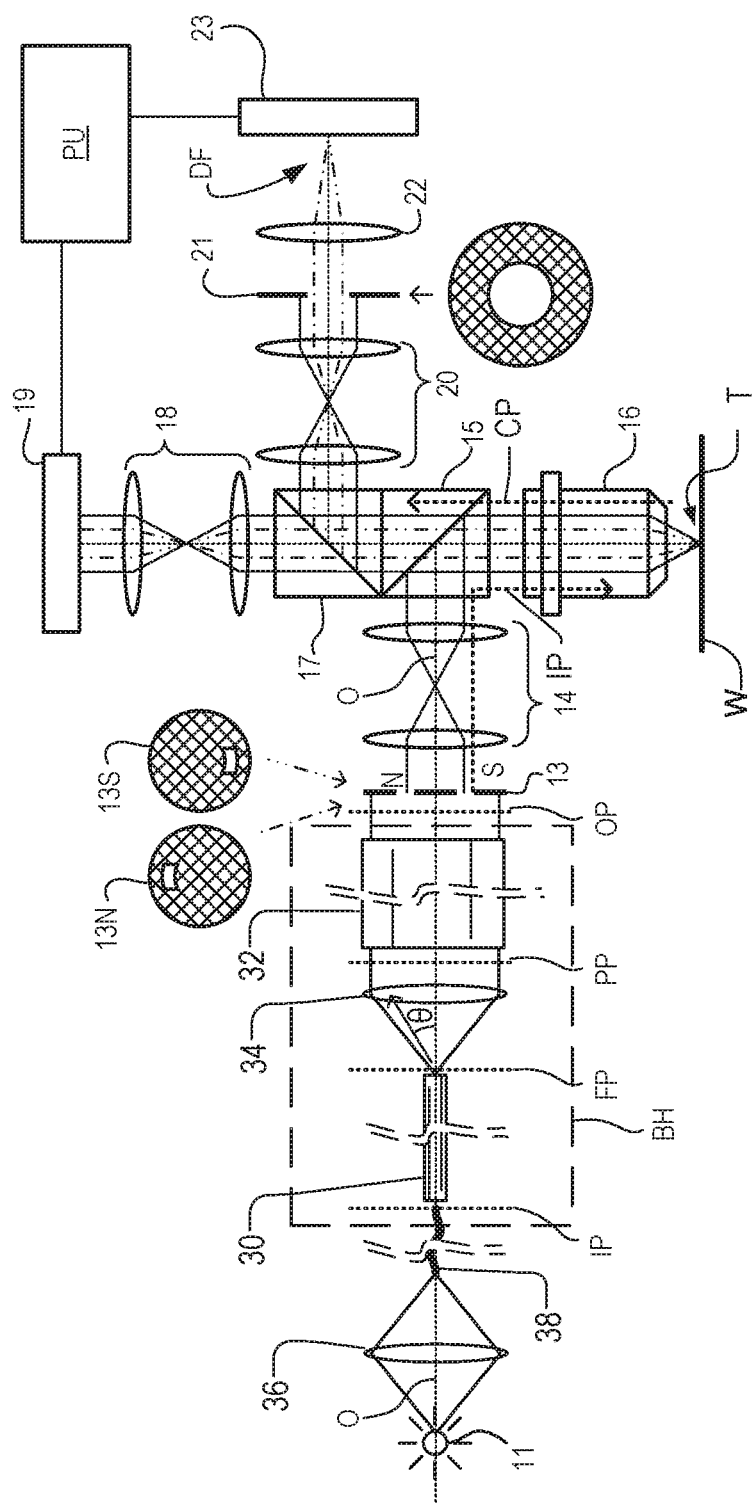
FIG. 2 comprises a schematic diagram of a metrology apparatus in which an illumination system includes a homogenizer according to a first embodiment of the present invention.

A metrology apparatus is shown in FIG. 2. The stand-alone metrology apparatus 240 and/or the integrated metrology apparatus 207 may comprise such a metrology apparatus, for example, or any other suitable metrology apparatus. A target structure T is formed on a substrate W and rays of inspection radiation are used to illuminate the target structure. The substrate W may be supported by a support (not shown). The metrology apparatus illustrated is of a type known as an angle-resolved scatterometer. An optical axis, which has several branches throughout the apparatus, is represented by a dotted line O. In this apparatus, light emitted by source 11 (e.g., a xenon lamp) is delivered into an illumination path IP via beam homogenizer BH (which will be described in detail below), aperture device 13, lenses 14 and beam splitter 15. Therefore, the angular range at which the radiation is incident on the substrate can be selected by defining a spatial intensity distribution in a plane that presents the spatial spectrum of the substrate plane, here referred to as a (conjugate) pupil plane. Aperture device 13 is located in such a plane, which is a back-projected image of the objective lens pupil plane. In the example illustrated, aperture device 13 can have different forms, labeled 13N and 13S, allowing different illumination modes to be selected. The illumination system in the illustrated example forms an off-axis illumination mode. In the first illumination mode, aperture plate 13N provides off-axis from a direction designated, for the sake of description only, as 'north'. In a second illumination mode, aperture plate 13S is used to provide similar illumination, but from an opposite direction, labeled 'south'. Other modes of illumination are possible by using different apertures, for example uniform illumination, and annular illumination. The rest of the pupil plane is desirably dark as any unnecessary light outside the desired illumination mode will interfere with the desired measurement signals.

Radiation scattered by the target structure is collected by objective lens 16 and directed back through beam splitter 15 into a collection path CP. Depending on the combination of the illumination mode, numerical aperture (NA) of the objective lens 16, the radiation wavelength, and the form of the target structure T, the collected radiation may include scattered radiation of zero order and/or higher orders of diffraction. A second beam splitter 17 divides the collection branch into two measurement branches. In a first measurement branch, optical system 18 forms a diffraction spectrum or scatter spectrum of the target on first sensor 19 (e.g. a CCD or CMOS sensor) using the zeroth and/or higher first order diffractive beams. Sensor 19 is located in another plane conjugate with the pupil plane of objective lens 16. Therefore each angle of scattered radiation hits a different point on the sensor, so that image processing can compare and contrast different parts of the scatter spectrum. The pupil plane image captured by sensor 19 can be used for many measurement purposes such as reconstruction.

In the second measurement branch, optical system 20, 22 forms an image of the target structure T on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image of the target formed on sensor 23 is formed only from the −1 or +1 first order beam. This second branch can be used for so-called dark-field imaging, which is particularly useful for measuring asymmetry-related properties of small targets.

The images captured by sensors 19 and 23 are output to processor PU which processes the image, the function of which will depend on the particular type of measurements being performed. Note that the term 'image' is used here in a broad sense. An image of the grating lines as such will not be formed, if only one of the −1 and +1 orders is present.

Beam Homogenizer

For metrology and other demanding applications, the characteristics of the radiation used to illuminate a target structure is generally carefully controlled. Therefore, in addition to an appropriate radiation source, an optical system is generally required for conditioning the radiation. In metrology, it is often desired that the beam of radiation should be as homogenous as possible. This is true for both field imaging and pupil imaging, in the scatterometers described above. For asymmetry measurements including measurements using the second measurement branch, it may be sufficient if the illumination is symmetrical. For angle-resolved scatterometry in the pupil plane, complete homogeneity is normally desirable.

It is therefore proposed to provide an optical system for conditioning a beam of radiation. The optical system in one example may be referred to as a beam homogenizer, and may for example be suitable for use in an illumination system of a metrology apparatus. In accordance with the principles of the present disclosure, the beam homogenizer comprises one or more optical mixing elements in an optical system, the optical system defining a path for a beam of radiation, the path including at least a first optical mixing stage, at least a second optical mixing stage, and at least one transformation stage, configured such that radiation entering the second optical mixing stage includes a transformed version of radiation exiting the first optical mixing stage. Different implementations of such an optical system will be described and illustrated in the following.

In the scatterometer of FIG. 2, a first example of beam homogenizer BH is illustrated, purely in schematic form. The beam homogenizer BH in this example comprises a first optical mixing element 30 and a second optical mixing element 32 in series, with a transforming element 34 positioned between them. Each optical mixing element 30, 32 may comprise an elongate element such as a chaotic mixing rod. The length of each element is generally several times its diameter, for example ten times or more. The elements in FIG. 2 are shown in cut-down form, for compactness of the drawing. The elements in FIG. 2 are shown arranged in a generally straight path, while in practice the path could be curved, for reasons of space. Where the diameter is small enough, one or both of the elements 30, 32 could be in the form of a flexible light guide, similar to an optical fiber.

Radiation from the illumination source 11 is optionally focused by a lens element 36 into an illumination fiber 38 which transports the radiation to the beam homogenizer BH, where it enters the first optical mixing element 30. In other embodiments, the lens element 36 and illumination fiber 38 may be considered part of the beam homogenizer BH. Other elements for selecting the wavelength and/or polarization of the radiation may be provided, but are not illustrated here, for simplicity. Most chaotic mixing elements will deliver unpolarized radiation, so that a polarizing element for selecting polarization of the illumination in illumination path IP will be positioned downstream of the beam homogenizer.

Various planes are labeled in the diagram of beam homogenizer BH, for ease of explanation. An input plane IP is positioned where the optical fiber 38 delivers radiation to an entry face of first optical mixing element 30. A field plane FP is shown where radiation exits the first optical mixing element 30. Transforming element 34 transforms the radiation from a field plane FP to a pupil lane PP. Transforming element 34 may have the form of a simple lens, with its focal plane exactly or approximately positioned in the field plane FP. Therefore an angular distribution of rays in the radiation exiting the first optical mixing element is transformed into a spatial distribution of radiation in the pupil plane PP, and vice versa. This is effectively a Fourier transform. The transformed version of the radiation exiting the first optical mixing element 30 enters the second optical mixing element in the vicinity of pupil plane PP. Radiation exits the second optical mixing element in the vicinity of an output plane OP, becoming the output of beam homogenizer BH. Other types of transform besides Fourier transforms may be envisaged, provided that at least partial transformation between the mixed and the unmixed coordinates is obtained. In a Fourier transform, transformation between the spatial distributions and angular distribution is obtained. Theoretically, a transforming element could be used which will exchange the unmixed angular coordinate ($\theta$) with the mixed angular coordinate ($\varphi$). The Fourier transform or other transform can be approximate. Mixing can be improved without being perfect.

As will be appreciated, the optical system illustrated provides a first optical mixing stage in the first optical mixing element 30, followed by a second optical mixing stage in the second optical mixing element 32. The transforming element 34 provides a transformation stage by which radiation entering the second optical mixing stage is a transformed version of the radiation exiting the first optical mixing stage. In this way, after passing through both optical mixing stages, the beam can be conditioned to be homogenized in both spatial an angular distributions, which is not achieved by a single optical mixing stage.

In the example application of the metrology apparatus of FIG. 2, for application in semiconductor device manufacture, the design of the optical system is such that the diameter of the beam in a field plane is smaller than the diameter of the beam in a pupil plane. For this reason, as illustrated, the first optical mixing element 30 may be different in diameter than the second optical mixing element 32. However, this illustration is purely schematic. It should be understood that the difference in beam diameters and mixing element diameters is not to scale in FIG. 2, and is exaggerated for clarity. The difference in diameter may be smaller or zero in practice. Furthermore, it is not necessary in practice to make the second mixing element significantly wider than the first. One way to avoid this is to make the transforming device have a very short focal length. Alternatively or in addition, the transforming device can be followed by a demagnifying device, such as a telescope (not shown). Similarly, the beam that exits the second mixing element can be manipulated at will to match the application, and avoid the need to use a wide mixing element. Purely by way of example, the diameter of each optical mixing element 30 might be a few hundred microns to a few millimeters. When one considers that the mixing rods should be ten or so times in length what they are in diameter, then it becomes clear that the beam homogenizer takes up substantial space in the design of the apparatus. Space saving embodiments will be described below.

In an embodiment, the optical mixing element 34 is an optical mixing element which uses chaotic billiard theory. Such an optical mixing element may be an elongate element comprising a cross-sectional shape (transverse to its length) which is neither a circle nor regular polygon. The optical mixing element may, for example, take any of the forms described and/or illustrated in the above-mentioned published patent application US2015/0003103, which is herein incorporated by reference in its entirety. However, the concepts described herein are not limited to these forms, and other forms could be used in their place. Examples of optical mixing elements will be described in greater detail below.

Figure 3:
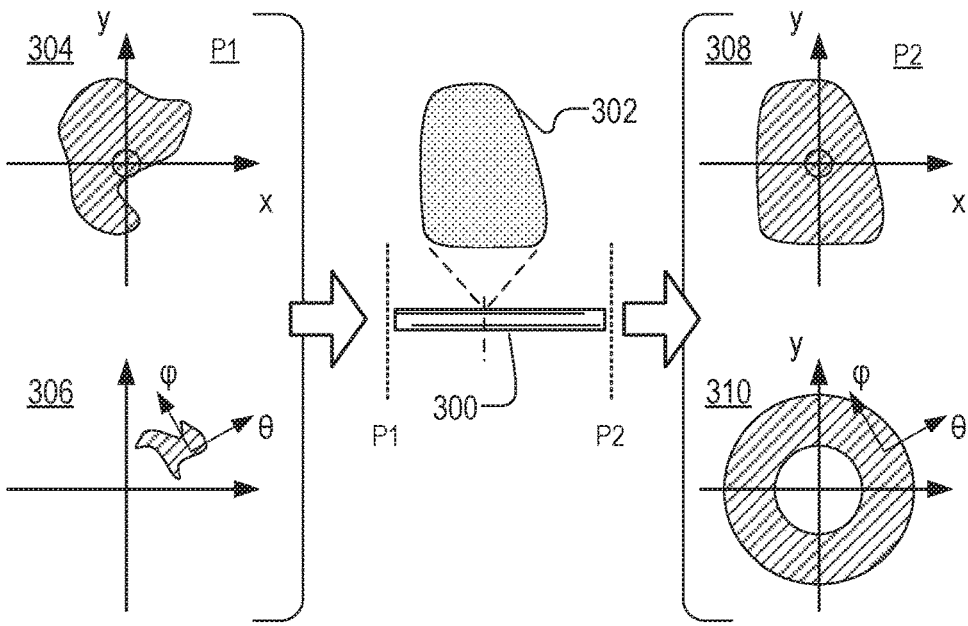
FIG. 3 illustrates the operation of an optical mixing element with a single stage of chaotic optical mixing.

FIG. 3 illustrates the homogenizing function of a single optical mixing element, such as might be used for an optical mixing stage in the present apparatus. Again the mixing element has the form of a chaotic mixing rod 300, of the type just described. In practice it may have a form even more elongated than that illustrated. The cross-sectional shape is irregular, as described, and is represented at 302. Plots 304-310 illustrate how such a mixing rod 300 homogenizes a radiation beam. Plot 304 shows the (arbitrary, non-uniform) spatial distribution of intensity of radiation in the beam in a plane P1, where it enters mixing rod 300. A small circle indicates the optical axis, lying at the origin of the plot, in which coordinates x and y are used to designate spatial position. Plot 306 shows the (arbitrary, non-uniform) angular distribution in the same plane. Angular coordinates $\theta$ and $\varphi$ are defined to describe the direction of a ray. Coordinate $\theta$ represents the radial angle of the ray, which is to say the deviation of the ray from a direction parallel to the optical axis O. The value of $\theta$ theoretically ranges from zero to $\pi/2$ (90 degrees), but in practice is limited to a smaller range proportional to the NA of the optical system. The other coordinate $\varphi$ may be referred to as the azimuthal direction, and is defined as an angle orthogonal to angle $\theta$. Angle $\varphi$ can range from 0 to $2\pi$. In the example plot 306, the angular distribution is limited to a particular sub-range of the possible values.

Plot 308 shows the spatial distribution of the same radiation in a plane P2, where it exits the mixing rod 300. The spatial mixing is such that the exit face of the mixing rod is uniformly filled with radiation. In terms of angular distribution, however, the plot 310 shows that the range of possible angles is still not uniformly filled. Specifically, while the direction of rays is uniformly distributed with respect to the azimuthal direction $\varphi$, the distribution in radial angle $\theta$ is not uniform. In this example, the radiation entering the mixing rod had no rays parallel or close to parallel with the optical axis O (i.e. no rays with $\theta$ close to zero). The mixed radiation exiting the mixing rod likewise has no rays with $\theta$ close to zero.

In conclusion, it is seen that the single mixing rod 300 homogenizes the radiation beam very well spatially, but only partially homogenizes the angular distribution. This partial angular homogenization breaks down into very good azimuthal homogenization, but poor or no radial homogenization. It will be understood that these plots are a simplified representation of the actual spatial and angular distributions of radiation, particularly with reference to the input plane IP. For example, the angular distribution of radiation in the input plane might vary between different positions in the plane, rather than being the same at all positions. Such variations are of course part of the reason why beam conditioning is needed in the first place. Such variations are reduced or eliminated by the action of the mixing element. The simplified representation is a valid representation of the real behavior, both in this example and in the examples below.

Figure 4:
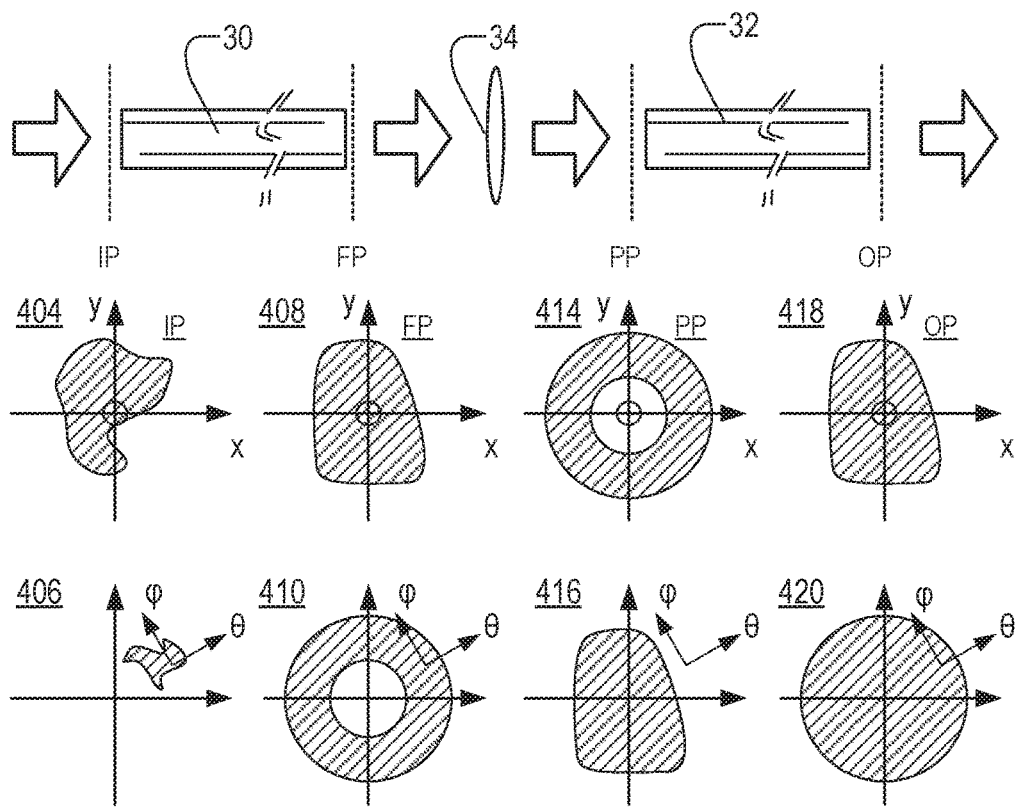
FIG. 4 illustrates schematically the operation of the homogenizer in the first embodiment of the present invention.

FIG. 4 illustrates how more complete homogenization of the radiation beam is achieved in the multi-stage arrangement of the beam homogenizer in the metrology apparatus of FIG. 2. The first optical mixing element 30 is provided in series with a second optical mixing element 32. The transforming element 34 is between them. The control of the angular radial profile may be such that the radiation is radially homogenized. Partially homogenized radiation entering a chaotic billiard optical mixing element 32 as described herein, will be further homogenized spatially and azimuthally, and therefore will be homogenized fully.

Plots 404 and 406 show the spatial distribution and angular distribution of radiation on entry to the first optical mixing element 30. Plots 408 and 410 show the spatial distribution and angular distribution of radiation on exit from the first optical mixing element 30. As might be expected, these plots are identical to the like-numbered plots 304-310 in the example of FIG. 3. Plots 414-420 show the effect of providing a transformation stage and a second mixing stage, in the form of transforming element (lens) 34 and second optical mixing element 32. Plots 414 and 416 show the spatial distribution and angular distribution of radiation on entry to the second optical mixing element 32. By the action of the transforming element 34, what was the spatial distribution at the exit of the first optical mixing element 30 (plot 408) becomes the angular distribution at the entry to the second optical mixing element 32 (plot 416). Similarly, the spatial distribution at the input to the second optical mixing element (plot 414) corresponds to the angular distribution at the exit of the first optical mixing element (plot 410).

Plots 418 and 420 show the spatial distribution and angular distribution of radiation on exit from the second optical mixing element 32. We have seen already that spatial mixing is thorough in such an optical mixing element. Therefore, while the non-uniform spatial distribution of plot 414 has been homogenized and made uniform at plot 418. Conversely, because the transformation stage delivered an already-homogenized angular distribution at the entry to the second stage (plot 416), the angular distribution at the exit of the second stage (plot 420) is also fully homogenized.

In summary, as a result of using two stages of mixing with a transformation stage in between, we see that both the spatial distribution (plot 418) and the angular distribution (plot 420) are fully homogenized, in both angles θ and φ. Additionally, the beam homogenizer of this type can be designed to operate without discarding large portions of the initially received radiation. Consequently a beam conditioning optical system of the type disclosed herein can be designed with high efficiency and high brightness, allowing a greater throughput of measurements, for a given measurement performance level.

Optionally, the metrology apparatus may include means for measuring the homogeneity of the beam. Such means already exist on some metrology apparatuses, and for example could include the camera 19 of FIG. 2, or any other such camera or sensor means.

Turning again to the optical mixing elements, this may comprise an elongated optical mixing element. The optical mixing element may be made of a transparent material like glass or plastic and may comprise an entry face and an exit face. At operation, a bundle of light rays is directed towards the entry face, wherein the bundle of light rays undergoes total internal reflection (TIR) at the interfaces towards the surrounding medium. After being reflected within the optical mixing element, the bundle of light rays exits the optical mixing element through the exit face. Instead of providing an optical mixing element of solid material and exploiting total internal reflection, the surfaces of the optical mixing element may simply be reflective.

Instead of a solid material, the optical mixing element may be a hollow tube, with reflective surfaces surrounding it. The shape and the manner of operation of the optical mixing element will hardly be changed. Considering the example of a hollow tube, it will be appreciated that the same principles may be applied in conditioning other types of radiation, such as acoustic (sound) radiation. The present disclosure therefore encompasses also a radiation conditioning system with radiation mixing stages and radiation mixing elements, and not only an optical system with optical mixing elements. The design of acoustic mixing elements, and acoustic transforming elements, for example, can be very similar in principle to the design of optical elements illustrated and described above. Optical radiation and optical systems are particularly disclosed herein purely as examples of particular current interest.

Any configuration and cross-sectional profile is possible which achieves chaotic mixing of the radiation as it internally reflects multiple times within the optical mixing elements 30 and/or 32. The number of possible designs are too numerous to list. The optical mixing element may comprise an elongated optical element arranged for homogenizing light, said optical mixing element comprising a transversal entry face and a transversal exit face, and having a cross section which has no stable paths, i.e., no paths for which a ray returns to the same x,y coordinate with the same direction (z is along the length of the optical mixing element). Of course, there may be differences in the degree of mixing between different cross section designs, with some cross sections mixing better than others (higher Lyaponov coefficients). For these, the optical mixing element can be shorter. As described in the published application US2015/0003103A1, the degree of mixing may be dependent on the position and/or direction of the radiation entering the optical mixing element, and this can be taken into account in the overall design.

In one class of embodiments, the cross section of the optical mixing element may have:
1) A periphery comprising at least one curved section; and
2) An absence of opposing edges which are parallel (a stable path would occur between such parallel edges, i.e., no mixing would happen).

In an embodiment, the total length of the curved section(s) constitutes at least 1% of the length of said perimeter, optionally much more.

In some embodiments, the cross section of the optical mixing element may have a perimeter shaped as a convex or concave shape (or partially both) and may comprise any number (including zero) of edges having zero curvature. For example the possible shapes include shapes that are not fully chaotic according to the criteria given above, but which perform a degree of mixing nevertheless. As mentioned above, a very thin element may even resemble an optical fiber, while still having an appropriate cross-sectional shape for a degree of chaotic mixing). For a fiber-like mixing element having a length of 3 meters, for example differences between shapes will become small.

The numbers of curved and non-curved portions of the perimeter do not have to be equal. Also sections of negative curvature (concave) are possible. Cross-sectional shapes can include, in addition to those described in US2015/0003103, shapes formed of inter alia two joined arcs (of the same or different curvature), an arc and straight line forming a "D" shape or similar, an arc and two straight lines in the form of a circle segment or similar, shapes based on polygons, but having curved vertices and/or one or more sides with negative curvature, or sections of both positive and negative curvature (e.g., "wavy"). It is to be understood that any shape which promotes mixing can be used, including shapes which achieve chaotic mixing.

Figure 5:
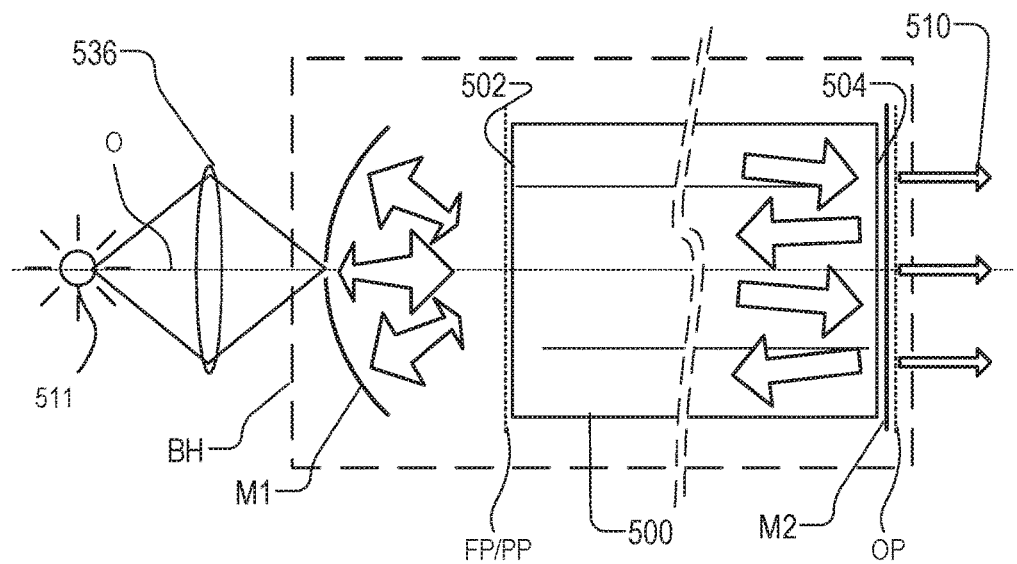
FIG. 5 illustrates schematically the configuration of a homogenizer in a second embodiment of the present invention.

FIG. 5 illustrates one alternative configuration of optical system, in which an optical path is defined with a first optical mixing stage, a transformation stage and a second optical mixing stage. In this design, actually multiple optical mixing stages are implemented using a single optical mixing element 500. The optical mixing element 500 may be of a form similar to the second optical mixing element 32 of FIGS. 2 and 4. That is to say, the diameter of the single mixing element should be the larger of the diameters of (i) the beam in a field plane FP and (ii) the beam in a pupil plane, PP. As illustrated, in this case, a first face 502 of optical mixing element 500 lies in the vicinity of a plane FP/PP which is both a field plane and a pupil plane. Face 502 serves as both an entry and an exit face. At the opposite end of the optical mixing element 500, a second face 504 serves as an entry face and an exit face. The second face 504, in this example, is positioned in the vicinity of the output plane OP.

In order to provide multiple optical mixing stages in this example, the beam of radiation is passed multiple times through the optical mixing element 500. In this example, element 500 is positioned in a reflecting cavity between two mirrors M1 and M2, as shown schematically. Radiation from source 511 is delivered through a lens 536 and optionally an optical fiber (not shown) through an aperture in first mirror M1, so as to enter for the first time the optical mixing element 500. The radiation passes back and forth through element 500 multiple times, so as to be mixed in multiple stages. First mirror M1 (in this example) is curved so as to be a focusing element, and this provides the transformation stage between stages. Second mirror M2 (in this example) is a planar mirror and reflects the majority of the radiation exiting second face 504 back into second face 504. Mirror M2 is partially transmissive, however, and a minor portion 510 of the radiation exiting from face 504 is transmitted through mirror M2 to form the conditioned output beam. In order to ensure that the majority of radiation passes through two or more optical mixing stages, mirror M2 may for example transmit less than 20%, for example approximately 10%, of the radiation exiting face 504 of element 500. The non-transmitted 80% or 90% is delivered back into face 504 to undergo at least one more stage of mixing. In this way, radiation on average will make ten or so round trips through optical mixing element 500, before being delivered to the illumination path of the metrology apparatus. The fact that the radiation makes a round trip in the optical mixing element may mean that the element can be shorter to achieve the same mixing.

At the other face 502 of element 500, again radiation exits the optical mixing element and is reflected my mirror M2 to re-enter the optical mixing element to provide the next stage of mixing. In order to effect an approximate Fourier transformation of the reflected radiation between exiting and re-entering element 500, a focal length of mirror M2 is set such that a focal point of the mirror lies on or near the entry face of the element 500. However, it is not critical what shape is the mirror, or whether the entry face 502 is at the focal point of the mirror or not: so long as the mirror is not imaging the face 502 onto itself, some transformation of coordinates will be achieved. Embodiments may also be envisaged in which the other mirror M2 is curved, or both mirrors. Plane mirrors could be used in combination with a separate transforming element such as a lens 34. Such a transforming element can be provided at either end or both ends of the cavity. One or both of the mirrors could be provided directly on the face 502, 504 of the optical mixing element. Either or both of the faces 502, 504 could itself be curved.

By this type of arrangement, first optical mixing stage, a second optical mixing stage, and in fact numerous optical mixing stages are provided in series, using a single optical mixing element 500. The mixing behavior of any two of these stages is the same as illustrated in FIG. 4. The mixing over multiple stages becomes even more thorough. Compared with the arrangement for FIGS. 2 and 4, a space saving may be obtained because there is no need to accommodate the length of two optical mixing elements. On the other hand, there may be less freedom to design each optical mixing element with different properties.

In an alternative configuration (not illustrated), multiple mixing stages are again implemented by multiple passes through a single optical mixing element. In this alternative, however, passes from the second face 504 to the first face 502 outside the optical mixing element, defining a "ring" topology, rather than a reflecting cavity. The ring may or may not be circular or polygonal in form. Optical mixing elements may be included in only one leg of the ring, or in more than one. Another way of viewing such a configuration is to regard the single optical mixing element as sub-divided into segments. The effect is the same. Optical mixing elements may be linear in form or curved. Instead of a partially transmissive reflecting element arranged to reflect the majority of the radiation back into the same face from which it exited the optical mixing element, as seen in FIG. 5, a partially transmissive element can be arranged to transmit a major fraction of the radiation into a path where it will eventually re-enter the first face of the optical mixing element, while reflecting a minor fraction into an output path. Alternatively, a partially transmissive element may transmit a minor fraction into an output path, while reflecting a major fraction into a path where it will eventually re-enter the first face of the optical mixing element.

As an aside, there is also disclosed an optical system for conditioning a beam of radiation in which one or more optical mixing elements are arranged in an optical system which passes the radiation through the element(s) multiple times, without a transforming element. Such an embodiment could for example have substantially the form shown in FIG. 5, but modified to have plane mirrors M1 and M2, instead of a curved mirror. One or both of these mirrors could be provided directly on the face 502, 504 of the optical mixing element, as mentioned above. While the mixing may not be enhanced in the same way as is achieved by inclusion of a transformation stage, mixing may be enhanced be the fact that effective length of the optical mixing element is multiplied by the (average) number of passes made by the radiation. Such an embodiment could also have the ring topology, mentioned above.

While the examples of FIGS. 2 to 5 are configured to provide a substantially uniform angular distribution, including in the radial direction, the optical system can actually be designed to achieve a customized, non-uniform angular distribution. Various techniques for doing this are illustrated in FIGS. 6 to 8.

Figure 6:
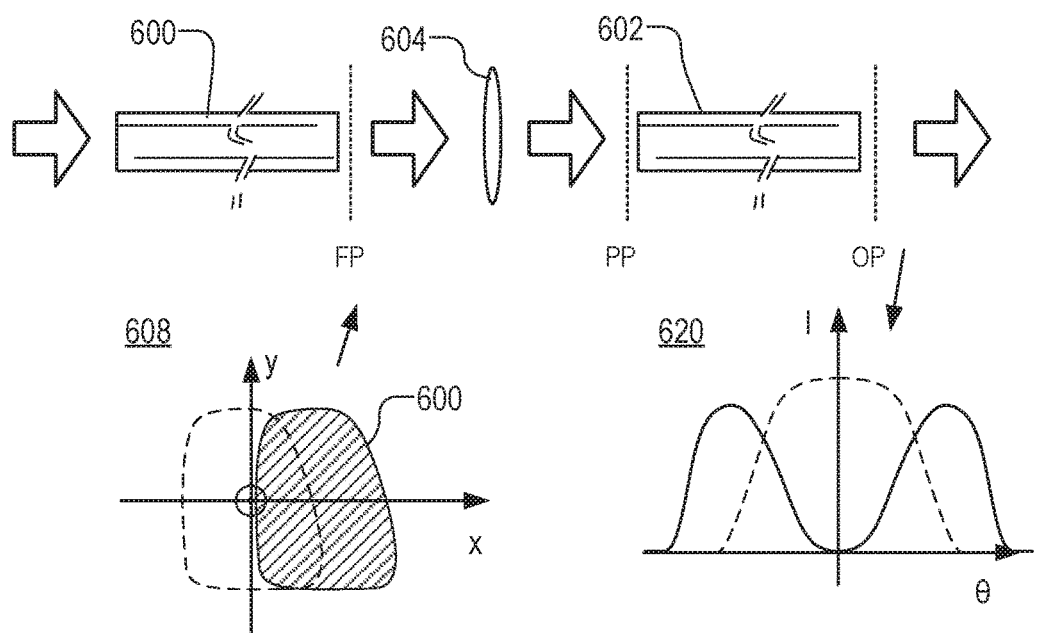
FIG. 6 illustrates the configuration and operation of a homogenizer in a modified embodiment of the invention.

In FIG. 6, a first optical mixing stage 600 is provided in series with a second optical mixing stage 602. A transformation stage 604 is provided so that the radiation entering the second optical mixing stage is a transformed version of radiation exiting the first optical mixing stage. These optical mixing stages and transformation stage can be implemented in any suitable way, including not only the configuration of FIG. 2 but also the cavity and ring configurations described with reference to FIG. 5.

In this example, first optical mixing stage 600 uses an optical mixing element that is shifted relative to the optical axis of the transformation stage 604. Plot 608 shows the spatial distribution of radiation at the exit of the first optical mixing stage (entry to the transformation stage 604), which then defines the angular distribution on entry to the second optical mixing stage 602. Because the range of ray angles is altered by the shift in the spatial distribution prior to the transformation, the angular distribution at the exit of the second optical mixing stage is no longer of the uniform distribution around zero, shown by the dotted curve in plot 620. Rather, the angular distribution shown in solid curve in plot 620 has a customized distribution, consisting in this example of a peak at radial angles away from the direction parallel to the optical axis. While this might seem like a reversion to the performance of a single optical mixing stage, illustrated in FIG. 3, in reality the designer of the apparatus has gained a lot of freedom to condition the beam with a desired spatial distribution and angular distribution. The shift can be made switchable or variable, for example. Thus, different illumination modes can be implemented for different types of task. For example, in a metrology apparatus such as the scatterometer of FIG. 2, one mode might be useful for measuring asymmetry-related parameters like overlay, while another mode is useful for measuring CD. The offset position of the exit face of the first optical mixing element is only one example of a parameter of the optical system that can be varied to change the illumination mode. Any of the optical elements can be moved in some way, or swapped for a different element.

Figure 7:
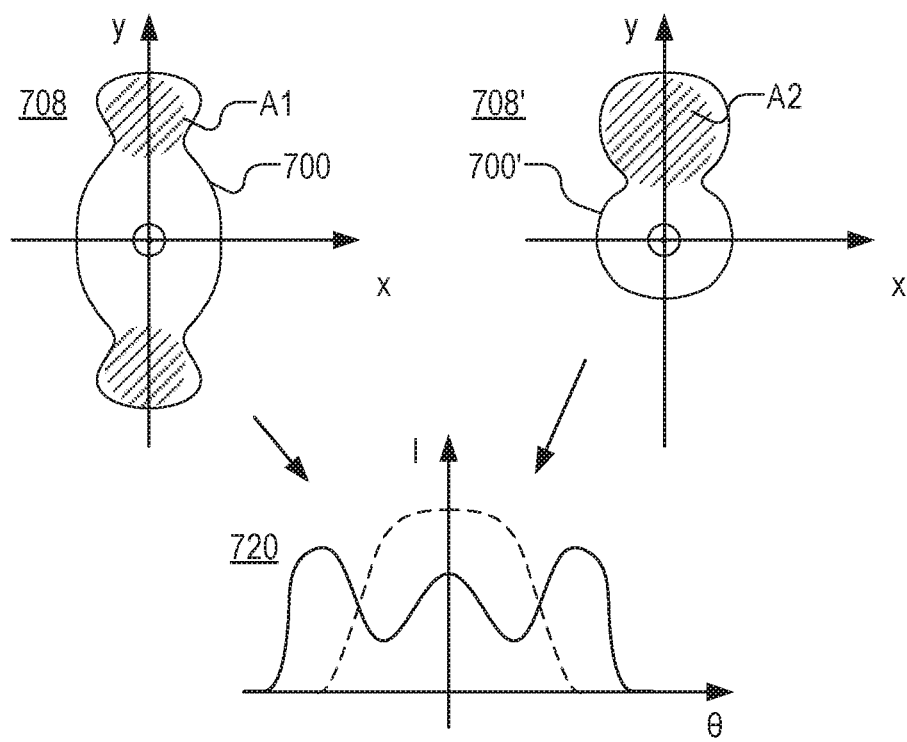
FIG. 7 illustrates the configuration and operation of a homogenizer in another modified embodiment of the invention.
Figure 8:
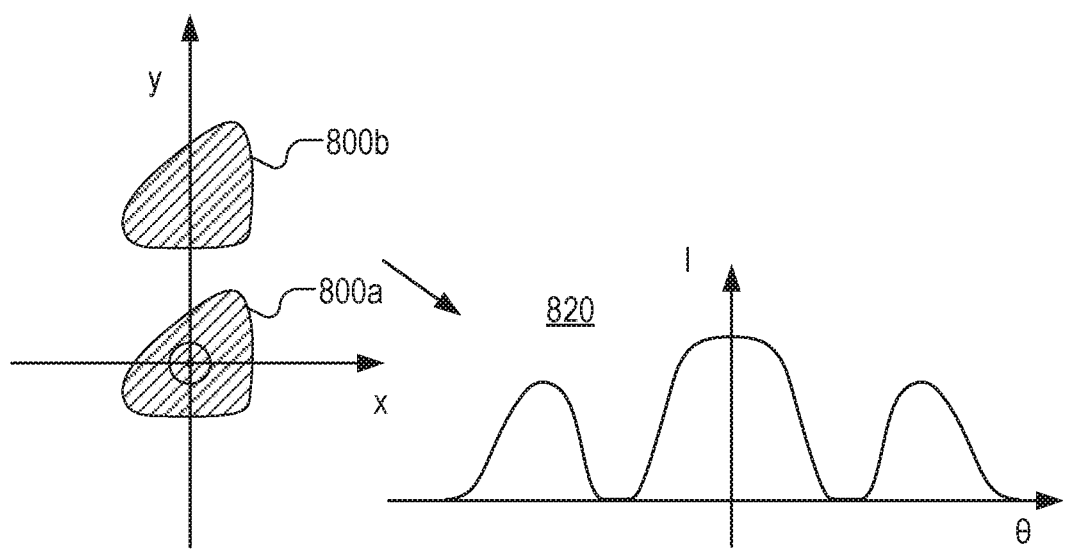
FIG. 8 illustrates the configuration and operation of a homogenizer in another modified embodiment of the invention.

FIG. 7 illustrates some other ways to achieve a non-uniform angular distribution of the form shown in plot 720. This distribution is achieved by choosing a special shape of the first mixing element 700, shown in plot 708. The exit face of a first optical mixing element 700 is shown in outline. It is symmetrical about the optical axis by has a lobed form. The shaded areas, when transformed prior to the second optical mixing stage, contribute to a higher intensity in extreme radial angles, while the shape also provides a peak of intensity in radial angles near zero. Since the second optical mixing stage homogenizes the angular distribution thoroughly in the azimuthal direction but not in the radial direction, the distribution of intensity over θ illustrated in plot 720 (solid curve) is obtained.

A similar angular distribution can be obtained using the different shaped exit face of the first optical mixing element 700' illustrated in plot 708'. This spatial distribution is not symmetrical. To achieve the same relationship between the central peak and the outer peaks in the plot 720, the single shaded area A2 in plot 708' is made twice the size of the shaded area A1 in plot 708. Since the angular distribution is homogenized in the azimuthal angle φ, the angular distribution at the output of beam homogenizer BH will be the same whether shape 700 or shape 700' is used.

FIG. 8 illustrates yet another way to achieve a similar non-uniform angular distribution at the output of the second optical mixing stage. In this example, two optical mixing elements are used in parallel to provide a first optical mixing stage with two distinct areas in the spatial distribution. One of the optical mixing elements 800a is arranged generally on and around the optical axis at the entry to the transformation stage, while another element 800b is arranged at an off-axis position. When these are transformed and homogenized in the azimuthal direction, the angular distribution illustrated in plot 820 is obtained.

When considering examples such as the one illustrated in FIG. 8 in the context of the cavity or ring-type implementation of FIG. 5, it will be understood that any and all of the individual parallel optical mixing elements can be considered as parts of a "common optical element". The optical system can be designed to implement mixing of radiation between these parallel optical mixing elements, as well as within each optical mixing element.

While the examples of FIGS. 6 to 8 provide customization of the angular distribution, other examples can be made that enable customization of the spatial distribution. One way to do this would be to add a transformation stage after in the optical path after the second optical mixing element.

Application

Figure 9:
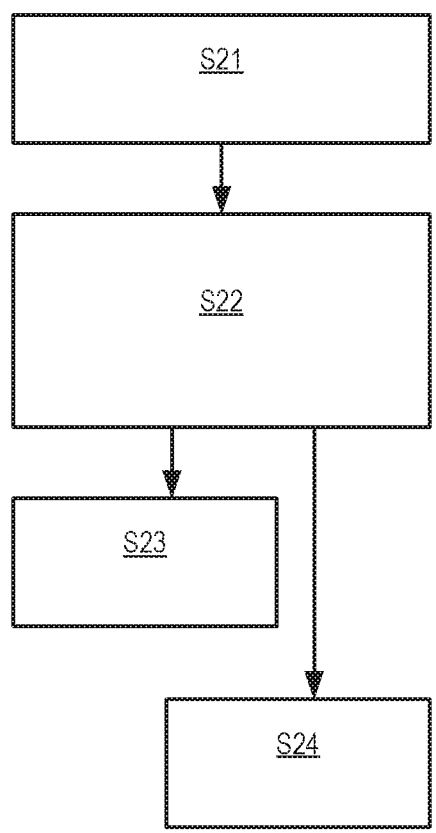
FIG. 9 is a flowchart illustrating use of the invention in methods of measuring and methods of manufacturing semiconductor devices.

FIG. 9 illustrates the application a metrology apparatus whose illumination system includes a beam homogenizer of the type disclosed herein, in the control of a lithographic manufacturing process of the type illustrated in FIG. 1. The steps will be listed here, and then explained in more detail:

S21: Process wafer to produce structures on substrate
S22: Measure CD and/or other parameter across substrate
S23: Update metrology recipe
S24: Update lithography and/or process recipe At step S21, structures are produced across a substrate using the lithographic manufacturing system. At S22, the metrology apparatus 240 and/or 207 and optionally other metrology apparatus and information sources are used to measure a property of the structures across the substrate. A property we are interested in may be one of CD (critical dimension), OVL (overlay) and/or EPE (edge placement error) for example. At step S23, optionally, metrology recipes and calibrations of the metrology apparatus are updated in light of the measurement results obtained.

At step S24, measurements of CD or other parameters are compared with desired values, and used to update settings of the lithographic apparatus and/or other apparatus within the lithographic manufacturing system. By providing a metrology apparatus with a better control of beam profile in both spatial and angular distributions, more accurate measurements can be obtained. This in turn can lead to better performance when the results of measurements are applied in further measurements and in further control of the lithographic apparatus.

As another example, an optical system for conditioning a beam of radiation according to the principles disclosed herein could also be applied in the illumination system of a lithographic apparatus LA.

Further embodiments according to the invention are described in below numbered clauses:

1. A system for conditioning a beam of radiation, the system defining a path for a beam of radiation, the path including at least a first mixing stage, at least a second mixing stage, and at least one transformation stage, configured such that radiation entering the second mixing stage includes a transformed version of radiation exiting the first mixing stage.

2. A system according to clause 1 wherein at least one angular coordinate of a distribution of said transformed version of radiation entering the second mixing stage is derived from a different angular coordinate and/or one or more spatial coordinates of a distribution of radiation exiting the first mixing stage.

3. A system according to clause 1 or 2 wherein a spatial distribution of the radiation exiting the first mixing stage is transformed at least partially into an angular distribution of the radiation entering the second mixing stage and an angular distribution of radiation exiting the first mixing stage is transformed at least partially into a spatial distribution of the radiation entering the second mixing stage.

4. A system according to clause 1, 2 or 3 wherein a radial angular coordinate of a distribution of said transformed version of radiation entering the second mixing stage is derived at least partially from an azimuthal angular coordinate of the distribution of radiation exiting the first mixing stage.

5. A system according to any preceding clause wherein said transformation stage is provided by one or more focusing elements.

6. A system according to any preceding clause wherein said transformed version is at least approximately a Fourier transformed version of the radiation exiting the first mixing stage.

7. A system according to any preceding clause wherein said system comprises at least one first mixing element providing the first mixing stage of the beam path and at least one second mixing element providing the second mixing stage of the beam path.

8. A system according to any preceding clause wherein said first mixing stage and said second mixing stage are provided by at least one common mixing element, said transformation stage being arranged to deliver at least a portion of radiation exiting the first mixing stage back into the common mixing element to enter the second mixing stage.

9. A system according to clause 8 wherein the system further includes a partially transmissive output element arranged to receive radiation exiting the common mixing element, to deliver a first fraction of said radiation into an output path to provide a conditioned output beam and to deliver a second fraction of said radiation again into the mixing element for the second mixing stage.

10. A system according to clause 9 wherein the second fraction of said radiation is reflected back into the common mixing element for the second mixing stage.

11. A system according to clause 9 or 10 wherein said first fraction is less than 20%, such that more than 80% of said radiation is delivered again into the mixing element.

12. A system according to any preceding clause configured so as to impart a defined non-uniform radial angular distribution in the beam when it exits the second mixing stage.

13. A system according to any preceding clause wherein the or each said mixing element comprises an entry face and an exit face, and has a perimeter shaped such that radiation travelling between said transversal entry face and the transversal exit face is chaotically mixed.

14. A system according to clause 13 wherein said perimeter comprises one or more curved sections and an absence of parallel opposing edges.

15. A system according to clause 14 wherein the total length of said one or more curved sections constitutes at least 1% of the length of said perimeter.

16. A system for conditioning a beam of radiation, the system defining a path for a beam of radiation, the path including at least a first mixing stage and at least a second mixing stage, wherein said first mixing stage and said second mixing stage are provided by at least one common mixing element, said system being arranged to deliver at least a portion of radiation exiting the first mixing stage back into the common mixing element to enter the second mixing stage.

17. A system according to clause 16 wherein the system further includes a partially transmissive output element arranged to receive radiation exiting the common mixing element, to deliver a first fraction of said radiation into an output path to provide a conditioned output beam and to deliver a second fraction of said radiation again into the mixing element for the second mixing stage.

18. A system according to clause 17 wherein the second fraction of said radiation is reflected back into the common mixing element for the second mixing stage.

19. A system according to clause 17 or 18 wherein said first fraction is less than 20%, such that more than 80% of said radiation is delivered again into the mixing element.

20. A metrology apparatus comprising:
   an illumination system for delivering inspection radiation to a structure under inspection; and
   a detection system configured to detect radiation arising from interaction of the structure with said inspection radiation,
   wherein the illumination system includes a radiation conditioning system according to any preceding clause.

21. A method of measuring a property of a structure, the method comprising:
   delivering inspection radiation to a structure under inspection; and
   detecting radiation arising from interaction of the structure with said inspection radiation; and
   determining a measurement of said property of the structure based on properties of the detected radiation,
   wherein the inspection radiation is conditioned using a radiation conditioning system according to any of clauses 1 to 19.

22. A method of manufacturing devices wherein a device pattern is applied to a series of substrates using a lithographic process, the method including measuring a property of at least one structure formed as part of or beside said device pattern on at least one of said substrates using a method according to clause 21, and controlling the lithographic process for later substrates in accordance with the result of the method.

23. A lithographic apparatus comprising:
   an illumination system for delivering radiation to a patterning device; and
   a projection system for using said radiation to transfer a pattern from the patterning device to a substrate,
   wherein said illumination system includes a radiation conditioning system according to any of clauses 1 to 19.

24. A method of manufacturing devices wherein a device pattern is applied to a substrate using a lithographic apparatus according to clause 23 and one or more chemical and/or physical processing steps are applied to the substrate to form functional device features in accordance with the applied pattern.

CONCLUSION

Although specific reference may have been made above to the use of embodiments of the invention in the context of lithography and metrology, it will be appreciated that the invention may be used in other applications.

Although specific reference has been made to optical radiation and an optical system for conditioning said radiation, the same principles may be applied in conditioning other types of radiation, such as sound radiation.

Any type of illumination system can be modified to include a beam conditioner (e.g. a beam homogenizer) of the type disclosed herein, without limitation to lithographic apparatus or metrology apparatus. Microscopes and medical imaging tools are examples. The beam of radiation may be conditioned and used for treating some material, not only for metrology inspection applications.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A system for conditioning a beam of radiation, the system comprising:
   first and second mixing stages; and
   a transformation focusing element whose focal plane is approximately positioned in a field plane of the system,
   wherein the first and second mixing stages and the transformation focusing element form a path for a beam of radiation,
   wherein radiation entering the second mixing stage includes a transformed version of radiation exiting the first mixing stage, and
   wherein a defined non-uniform angular distribution is imparted in the beam when it exits the second mixing stage.

2. The system of claim 1, wherein:
   at least one angular coordinate of a distribution of the transformed version of radiation entering the second mixing stage is derived from a different angular coordinate and/or one or more spatial coordinates of a distribution of radiation exiting the first mixing stage.

3. The system of claim 1, wherein:
   a spatial distribution of the radiation exiting the first mixing stage is transformed at least partially into an angular distribution of the radiation entering the second mixing stage; and
   an angular distribution of the radiation exiting the first mixing stage is transformed at least partially into a spatial distribution of the radiation entering the second mixing stage.

4. The system of claim 1, wherein:
   a radial angular coordinate of a distribution of the transformed version of radiation entering the second mixing stage is derived at least partially from an azimuthal angular coordinate of the distribution of radiation exiting the first mixing stage.

5. The system of claim 1, wherein the transformation focusing element comprises a lens.

6. The system of claim 1, wherein the transformed version is approximately a Fourier transformed version of the radiation exiting the first mixing stage.

7. The system of claim 1, wherein:
   a first mixing element comprises the first mixing stage of the beam path; and
   a second mixing element comprises the second mixing stage of the beam path.

8. The system of claim 7, wherein:
   at least one of the first and second mixing elements comprises an entry face and an exit face, and has a perimeter shaped such that radiation travelling between a transversal entry face and a transversal exit face is chaotically mixed.

9. The system of claim 8, wherein the perimeter comprises one or more curved sections and an absence of parallel opposing edges.

10. The system of claim 9, wherein a total length of the one or more curved sections constitutes at least 1% of the length of the perimeter.

11. The system of claim 1, wherein the first optical mixing stage comprises a first mixing element that is shifted relative to an optical axis of the transformation focusing element.

12. A system for conditioning a beam of radiation, the system comprising:
    first and second mixing stages,
    wherein the first and second mixing stages are provided by at least one common mixing element,
    wherein the first and second mixing stages define a path for a beam of radiation, and
    wherein at least a portion of radiation exiting the first mixing stage is delivered back into the common mixing element to enter the second mixing stage.

13. The system of claim 12, further comprising:
    a partially transmissive output element configured to receive radiation exiting the common mixing element, to deliver a first fraction of the radiation into an output path to provide a conditioned output beam, and to deliver a second fraction of the radiation again into the common mixing element for the second mixing stage.

14. The system of claim 13, wherein the second fraction of the radiation is reflected back into the common mixing element for the second mixing stage.

15. The system of claim 13, wherein the first fraction is less than 20%, such that more than 80% of the radiation is delivered again into the mixing element.

16. A metrology apparatus comprising:
an illumination system configured to deliver inspection radiation to a structure under inspection; and
a detection system configured to detect radiation arising from interaction of the structure with the inspection radiation,
wherein the illumination system includes a radiation conditioning system comprising:
   first and second mixing stages; and
   a transformation focusing element whose focal plane is approximately positioned in a field plane of the system,
   wherein the first and second mixing stages and the transformation focusing element form a path for a beam of radiation,
   wherein radiation entering the second mixing stage includes a transformed version of radiation exiting the first mixing stage, and
   wherein a defined non-uniform angular distribution is imparted in the beam when it exits the second mixing stage.

17. A method of measuring a property of a structure, the method comprising:
delivering inspection radiation to a structure under inspection;
detecting radiation arising from interaction of the structure with the inspection radiation;
determining a measurement of the property of the structure based on properties of the detected radiation; and
conditioning the inspection radiation comprising:
   using first and second mixing stages provided by at least one common mixing element,
   using the first and second mixing stages to define a path for a beam of radiation, and
   wherein at least a portion of radiation exiting the first mixing stage is delivered back into the common mixing element to enter the second mixing stage.

18. A method of manufacturing devices, comprising:
applying a device pattern to a series of substrates using a lithographic process;
measuring a property of at least one structure formed as part of or beside the device pattern on at least one of the substrates using a method comprising:
   delivering inspection radiation to a structure under inspection;
   detecting radiation arising from interaction of the structure with the inspection radiation;
   determining a measurement of the property of the structure based on properties of the detected radiation; and
   conditioning the inspection radiation comprising:
      using a transformation focusing element whose focal plane is approximately positioned in a field plane of the system; and
      forming a path for a beam of radiation using first and second mixing stages and the transformation focusing element,
      wherein radiation entering the second mixing stage includes a transformed version of radiation exiting the first mixing stage; and
      wherein a defined non-uniform angular distribution is imparted in the beam when it exits the second mixing stage; and
controlling the lithographic process for later substrates in accordance with the result of the method.

19. A lithographic apparatus comprising:
an illumination system configured to deliver radiation to a patterning device; and
a projection system configured to use the radiation to transfer a pattern from the patterning device to a substrate,
wherein the illumination system includes a radiation conditioning system comprising:
   first and second mixing stages; and
   a transformation focusing element whose focal plane is approximately positioned in a field plane of the system,
   wherein the first and second mixing stages and the transformation focusing element form a path for a beam of radiation,
   wherein radiation entering the second mixing stage includes a transformed version of radiation exiting the first mixing stage, and
   wherein a defined non-uniform angular distribution is imparted in the beam when it exits the second mixing stage.

20. A method of manufacturing devices, comprising:
applying a device pattern to a substrate using a lithographic apparatus comprising:
   using an illumination system to deliver radiation to a patterning device;
   using a projection system to transfer a pattern from the patterning device to a substrate; and
   using the illumination system to condition the radiation, the conditioning comprising:
      forming a path for a beam of the radiation using first and second mixing stages and a transformation focusing element, the transformation focusing element having a focal plane positioned approximately in a field plane of a system,
      wherein radiation entering the second mixing stage includes a transformed version of radiation exiting the first mixing stage, and
      wherein a defined non-uniform angular distribution is imparted in the beam when it exits the second mixing stage; and
applying one or more chemical and/or physical processing steps to the substrate to form functional device features in accordance with the applied pattern.

* * * * *